United States Patent [19]

Dupuis

[11] Patent Number: 5,830,438
[45] Date of Patent: Nov. 3, 1998

[54] COSMETIC HAIR CARE FOAM COMPOSITION

[75] Inventor: Christine Dupuis, Paris, France

[73] Assignee: L'Oreal, Pairs, France

[21] Appl. No.: 804,032

[22] Filed: Feb. 21, 1997

[30] Foreign Application Priority Data

Feb. 21, 1996 [FR] France ................................. 96 02125

[51] Int. Cl.$^6$ ................................ A61K 7/06; A61K 7/11
[52] U.S. Cl. ........................ 424/45; 424/401; 424/70.1; 424/70.11; 424/70.13; 424/70.16; 424/70.17; 424/70.19; 424/70.21; 424/70.27; 424/70.28; 424/43; 514/945; 514/975
[58] Field of Search .................... 424/401, 45, 70.11, 424/70.13, 70.19, 70.21, 70.27, 43, 70.16, 70.28, 70.17, 70.1

[56] References Cited

U.S. PATENT DOCUMENTS

| | | | |
|---|---|---|---|
| 4,985,487 | 1/1991 | Shih et al. | 524/548 |
| 5,645,609 | 7/1997 | Andrean et al. | 8/405 |

FOREIGN PATENT DOCUMENTS

| | | |
|---|---|---|
| 172713 | 2/1986 | European Pat. Off. . |
| 2098624 | 11/1982 | United Kingdom . |
| 91/03521 | 3/1991 | WIPO . |

*Primary Examiner*—Thurman K. Page
*Assistant Examiner*—James M. Spear
*Attorney, Agent, or Firm*—Nixon & Vanderhye, P.C.

[57] ABSTRACT

Cosmetic composition for hair-care foam containing, in a cosmetically-acceptable vehicle, a mixture (i) of at least one cationic polymer chosen from the cationic celluloses, cellulose ethers containing quaternary ammonium groups, quaternized or non-quaternized vinylpyrrolidone/ dialkylaminoalkyl acrylate or methacrylate copolymers, and quaternized or non-quaternized vinyl pyrrolidone/ dialkylaminoalkyl acrylamide or methacrylamide copolymers; and (ii) of at least one amphoteric polymer chosen from polymers deriving from the copolymerization of an alkylvinylether and maleic anhydride, an N-vinyl lactam and maleic anhydride, and an alkylvinylether, maleic anhydride and an N-vinyl lactam, said polymers being modified by an N,N-dialkylaminoalkylamine or an N,N-dialkylaminoalkanol. This composition possesses good foaming properties and leads to the formation of a foam having excellent cosmetic properties.

16 Claims, No Drawings

COSMETIC HAIR CARE FOAM COMPOSITION

This present application claims priority to FR 96 02125 filed Feb. 21, 1996, the entire contents of which is incorporated herein by reference.

The present invention concerns a composition used to prepare a hair-care foam comprising at least one cationic polymer and at least one amphoteric polymer possessing effective foaming properties and yielding a foam having excellent cosmetic properties.

In accordance with the invention, the term "foaming properties" signifies properties yielding a foam which meets consumers' demands for expansion, stiffness, and stability properties. This foam must, moreover, have a density of less than 0.4, and preferably less than 0.25 g/cm3 (the working conditions for such an analysis will be described below in greater detail).

Patent No. FR-82.07996 (2,505,348) describes an aerosol foam composition containing at least one cationic polymer and/or anionic polymer in an aqueous solvent medium without addition of a foaming surface-active compound, the cationic and/or anionic polymers having foaming properties which, in combination with the solvent medium, yield a short-lived foam which rapidly disappears in contact with the hair without leaving any residual foam.

This patent also describes a combination of an anionic and/or cationic polymer with an amphoteric polymer.

Among known cationic polymers, some possess poor foaming properties, thus making it necessary to add to them an amphoteric polymer with foaming properties sufficient to ensure that the resulting combination gives a foam meeting the requisite cosmetic requirements.

Accordingly, Patent No. FR-82.07996 recommends, in particular, to combine with a cationic polymer various amphoteric polymers, including the N-octylacrylamide/acrylic acid/t-butylaminoethyl methacrylate copolymer ("Amphomer" made by the National Starch Company), which is known to exhibit good foaming properties. However, this type of amphoteric polymer possesses unsatisfactory cosmetic properties, since it imparts to the hair only a medium level of softness, and even produces a rustling sound when the hair is detangled (see especially Ch. Zviak, The Science of Hair Care, p. 163: "Amphoteric Resins").

It has now been unexpectedly and surprisingly discovered that the combination of certain selected cationic polymers with a well-defined class of amphoteric polymers, which, taken separately, exhibit poor foaming properties, produced a marked synergistic effect as regards the expansion, stiffness, and stability of the foam produced, which, furthermore, had a density advantageously less than 0.25 g/cm3. Furthermore, this combination provides advantageous cosmetic properties as regards the softness and detangling of the hair, in particular.

Thus, the present invention concerns a cosmetic hair-care foam composition containing a combination of polymers and characterized by the fact that it contains, in a cosmetically-suitable vehicle, a mixture (i) of at least one cationic polymer chosen from the cationic celluloses, cellulose ethers containing quaternary ammonium groups, quaternized or non-quaternized vinyl pyrrolidone/ dialkylaminoalkyl acrylate or methacrylate copolymers, quaternized or non-quaternized vinyl pyrrolidone/ dialkylaminoalkyl acrylamide or methacrylamide copolymers; and (ii) of at least one amphoteric polymer chosen from polymers deriving from the copolymerization of an alkylvinylether and maleic anhydride, an N-vinyl lactam and maleic anhydride, or an alkylvinylether, maleic anhydride and an N-vinyl lactam, said polymers being modified by an N,N-dialkylaminoalkylamine or an N,N-dialkylaminoalkanol.

When the cationic polymer in the compositions according to the invention is a cationic cellulose, the latter is preferably chosen from cellulose derivatives grafted with a water-soluble monomer in the form of quaternary ammonium, such as those described in U.S. Pat. No. 4,131,576 and, in particular, hydroxyalkylcelluloses such as hydoxymethyl-, hydoxyethyl- and hydroxypropylcelluloses grafted with a salt of methacryloyl-ethyltrimethyl ammonium, methacrylamidopropyltrimethyl ammonium, or dimethyldiallyl ammonium. These products can be purchased, for example under the tradenames "Celquat L 200" and "Celquat H 100" made by the National Starch Company.

When the cationic polymer in the compositions according to the invention is a cellulose ether containing quaternary ammonium groups, the latter is preferably chosen from those described in Patent No. FR-1,492,597, and, most especially, quaternary ammonium hydroxyethylcelluloses having reacted with an epoxy substituted by a trimethyl ammonium group. Polymers of this kind are sold, for example, under the tradenames "JR 400," "JR 125," and "JR 30M", or under the names "LR 400" and "LR 30M" by the Union Carbide Corporation.

Finally, when the cationic polymer in the compositions according to the invention is a quaternized or non-quaternized vinyl pyrrolidone dialkylaminoalkyl acrylate or methacrylate copolymer or a quaternized or non-quaternized vinyl pyrrolidone/dialkylaminoalkylamino acrylate or methacrylate copolymer, the former is preferably chosen from those described in Patents Nos. FR-71.03017 (2,077,143) and FR-78.17320 (2,393,573), such as those sold under the tradenames "Gafquat 734," "Gafquat 755," or under the names "Copolymer 845, 958, and 937" by the ISP Corporation. Preference is also given to the quaternized vinyl pyrrolidone dimethylaminopropyl methacrylamide, such as that sold by the ISP Corporation under the tradename "Gafquat HS 100."

According to a preferred embodiment of the invention, the cationic polymer is a cationic cellulose.

Preferably, the cationic polymer has a weight average molecular mass of between approximately 500 and $5 \times 10^6$, and more especially between 10,000 and $10^6$.

In accordance with the definition of amphoteric polymers given above, these polymers may belong to the following three groups:

(a) the first group corresponds to the amphoteric polymers basically consisting of the following repeating units:

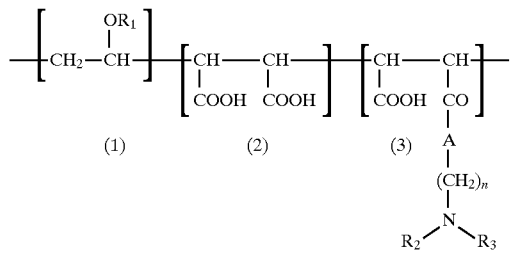

in which:

R1 is a $C_1$–$C_6$ alkyl,

R2 and R3 whether identical or different, represent a $C_1$–$C_8$ alkyl,

A is an atom of oxygen or NH, and n=2 to 10.

Preferably, the units corresponding to formula (1), (2), and (3) are present in the following molar proportions:

(1) from 10 to 90%, and preferably from 20 to 50%,
(2) from 5 to 90%, and preferably 15 to 50%,
(3) from 5 to 90%, and preferably from 15 to 50%.

According to a special embodiment, the amphoteric polymers in the (a) group are those in which the radicals R1, R2, and R3 represent —CH$_3$, A is NH, and n=3.

(b) The second group includes amphoteric copolymers basically consisting of the following repeating units:

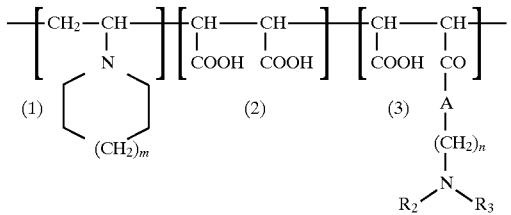

where:

R2, R3, A, and n have the same meanings as those given above, and m is 0, 1, or 2.

Preferably, the units in formulae (1), (2), and (3) are present in the following molar proportions:

(1) from 5 to 90%, and preferably 10 to 70%,
(2) from 5 to 90%, and preferably 10 to 70%,
(3) from 5 to 90%, and preferably 10 to 70%.

(c) The third group includes amphoteric polymers basically consisting of the following repeating units:

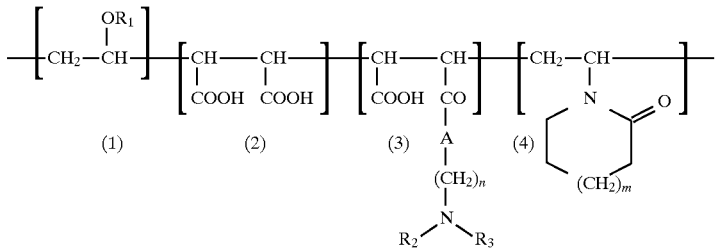

where:

R1, R2, R3, A, m and n have the same meanings as those given above.

Preferably the units in formulae (1), (2), (3), and (4) are present in the following molar proportions:

(1) from 5 to 90%, and preferably 10 to 70%,
(2) from 5 to 90%, and preferably 10 to 70%,
(3) from 5 to 90%, and preferably 10 to 70%,
(3) from 5 to 90%, and preferably 10 to 70%,
(4) from 5 to 90%, and preferably 10 to 70%.

According to a special embodiment, the amphoteric polymers belonging to the (c) group are those in which the radicals R1, R2, and R3 represent —CH$_3$, A is NH, n=3, and m=2.

In the amphoteric polymers in groups (a), (b) and (c), the units corresponding to formula (3) may potentially exist in zwitterionic form.

Preferably, the amphoteric polymers specified above have a weight average molecular mass of between 500 and 5×10$^6$.

The amphoteric polymers according to the invention include, for example, those sold by the ISP Corporation under the tradenames "ACV-4013" and "ACV-4014" and the product sold by the ISP Corporation under the name "Vinyl Caprolactam Modified Amphoteric Gantrez," which will be specified below under the name "VC MAG."

In the hair-care foam compositions according to the invention, the proportion of cationic and amphoteric polymers may range between 0.05 and 20%, preferably between approximately 0.2 and 10%, and, more especially, between about 0.25 and 5% of the total weight of the composition.

The weight ratio of the cationic to the amphoteric polymer preferably ranges between approximately 10/90 and 90/10, and, more particularly, between about 20/80 and 80/20.

The solvent used in the compositions according to the invention must, after expansion of the composition, allow formation of a foam possessing good cosmetic properties and ease of spreadability on the hair.

The solvent preferably consists of water, but can also be made from a hydroalcoholic mixture of a C$_1$–C$_4$ alcohol chosen, preferably, from ethanol or isopropanol.

When, for example, use is made of a hydroalcoholic solution, the proportion of alcohol preferably does not exceed 50% and is preferably lower than 30% of the total weight of the composition.

In addition to the specific cationic and amphoteric polymers described above, the composition in question may also contain conventional cosmetic additives which do not of themselves possess any foaming capability, such as coloring agents used to color the composition or the hair, preservatives, sequestering agents, pH-adjustment agents, perfumes, silicones, proteins, sunscreens, and treating agents and/or electrolytes, preferably alkaline metal salts.

The pH of the compositions according to the invention is preferably adjusted to a value of between approximately 4 and 9, and preferably between about 6 and 8.

Among these pH-adjustment agents, mention may be made of 2-amino-2-methyl-1-propanol, monoethanolamine, triethanolamine, triisopropanolamine, sodium hydroxide, and potassium hydroxide.

The compositions according to the invention may be packaged in non-aerosol containers, in particular those of the "squeeze bottle" type, but aerosol packaging is preferred.

When the composition according to the invention is packed in an aerosol container, it also contains a propellant chosen from compressed air, carbon dioxide, nitrogen, nitrous oxide, butane, isobutane, dimethylether, and chlorinated and/or fluorinated hydrocarbons and mixtures thereof.

The propellant concentration normally ranges between 1 and 20% of the total weight of the composition, and, preferably between 5 and 15%.

Internal pressure in the aerosol container generally ranges from approximately 1 to 4 bars ($10^5$ to $4\times10^5$ pa).

Any type of container and valve system for aerosol foam is suited to implementation of the invention according to this embodiment.

SYNERGY TESTS

To illustrate the surprising synergistic effect obtained by combining the specific cationic and amphoteric polymers described above, the tests detailed below were conducted and the results recorded in Table I.

To this end, aerosol foam containers were prepared by pressurizing a mixture containing, in a weight proportion of the total weight of the mixture, 10% propellant consisting of a mixture of isobutane/propane/butane sold under the tradename "Aérogaz 3.2N" by the Elf Aquitaine Company, and 90% of an aqueous solution containing 1% of a polymer chosen from a cationic polymer, an amphoteric polymer, and a mixture of these polymers.

Once expelled from the aerosol container, the foam was submitted to a five-judge panel for evaluation of the criteria of expansion, rigidity, and stability on a scale of 0 to 6, 0 corresponding to low criteria levels and 6 signifying excellent levels. For each criterion examined, the average of the grades assigned by the judges was calculated.

Furthermore, the density of each foam was measured under the following conditions.

The tests were conducted 24 hours after pressurization of the aerosol mixture in a room cooled to 200° C.±1° C., the equipment and sample being cooled to this same temperature. A cylindrical cup having volume V was weighed when empty (weight=P1), then filled directly with the foam produced by the aerosol. Each aerosol container was vigorously shaken before use, in order to emulsify the propellant gas.

To ensure uniform distribution of the foam in the cup, the aerosols were used upside down in an even rotating motion.

Once the foam stopped expanding, the foam was leveled immediately and quickly using a wide spatula, and the cup was weighed again (weight=P2).

The density of the foam was calculated using the following formula:

$$\text{density at } 20° \text{ C.} = \frac{P_2 - P_1}{V}$$

Three calculations were made for each aerosol composition, the value finally selected being the average of these calculations (in g/cm$^3$).

To conform to the invention, the foam had to have a density of less than 0.4, and preferably less than 0.25 g/cm$^3$.

TABLE I

| Cationic and/or amphoteric polymer | Polymer concentration (% AS)* | Expansion (0–6)** | Stiffness (0–6)** | Stability (0–6)** | Density (g/cm$^3$) |
|---|---|---|---|---|---|
| Celquat L200 (cationic) | 1 | 3.4 | 2.8 | 3.0 | 0.075 |
| ACV-4013 (amphoteric) | 1 | 1.2 | 0.7 | 0.6 | >0.25 |
| VC MAG (amphoteric) | 1 | 3.8 | 0.5 | 0.6 | >0.25 |
| Celquat L200 (cationic) + ACV-4013 (amphoteric) | 0.5 0.5 | 4.7 | 4.3 | 4.9 | 0.066 |
| Celquat L200 (cationic) + VC MAG (amphoteric) | 0.5 0.5 | 5.2 | 4.4 | 5.4 | 0.041 |

*(% AS) = % by weight of active substance
**0 = very poor → 6 = very good

The results in Table I clearly show the surprising synergistic effect produced when a cationic polymer was combined with an amphoteric polymer such as those specified above, according to the object of the invention.

The following examples illustrate the invention.

EXAMPLE 1

Hairdressing Foam

An aerosol foam was prepared by mixing the following ingredients:

| | |
|---|---|
| Celquat L200 cationic polymer | 0.8% AS |
| VC MAG amphoteric polymer | 0.5% AS |
| 2-amino-2-methyl-1-propanol | q.s. pH = 8 |
| Demineralized water | q.s.p. 100 g |

The composition as prepared, was placed in an aerosol container with Aérogaz 3.2N as the propellant in proportions of 95% and 5% respectively of the total weight of the mixture. Then, a suitable valve was attached to the aerosol container.

The foam obtained after depressurization was of excellent quality and had a density of 0.035 g/cm$^3$ according to the test described above.

EXAMPLE 2

Hairdressing Foam

An aerosol foam was prepared by mixing the following ingredients:

| | |
|---|---|
| Gafquat 734 cationic polymer | 1% AS |
| VC MAG amphoteric polymer | 1% AS |
| Absolute ethanol | 8.2 g |
| 2-amino-2-methyl-1-propanol | q.s. pH = 8 |
| Demineralized water | q.s.p. 100 g |

The composition as prepared, was placed in an aerosol container with Aérogaz 3.2N as the propellant in proportions of 90% and 10% respectively of the total weight of the mixture, and a suitable valve was attached to the aerosol container.

The foam obtained after depressurization was of excellent quality and had a density of 0.03 g/cm$^3$ according to the test described above.

EXAMPLE 3

Hairdressing Foam

An aerosol foam was prepared by mixing the following ingredients:

| | |
|---|---|
| Gafquat 755 cationic polymer | 1% AS |
| ACV 4013 amphoteric polymer | 1.5% AS |
| 2-amino-2-methyl-1-propanol | q.s. pH = 7 |
| Demineralized water | q.s.p. 100 g |

The composition as prepared, was placed in an aerosol container with Aérogaz 3.2N used as the propellant in proportions of 90% and 10% respectively of the total weight of the mixture, and a suitable valve was attached to the aerosol container. The foam obtained after depressurization was of excellent quality and had a density of 0.075 g/cm$^3$ according to the test described above.

The entire contents of references cited herein are incorporated by reference.

What is claimed is:

1. A cosmetic composition for hair-care foams containing in a cosmetically-suitable vehicle, a mixture (i) of at least one cationic polymer selected from the group consisting of cationic celluloses, cellulose ethers containing quaternary ammonium groups, quaternized or non-quaternized vinyl pyrrolidone/dialkylaminoalkyl acrylate or methacrylate copolymers, and quaternized or non-quaternized vinyl pyrrolidone/dialkylaminoalkyl acrylamide or methacrylamide copolymers; and (ii) of at least one amphoteric polymer selected from the group consisting of polymers deriving from the copolymerization of an alkylvinylether and maleic anhydride, an N-vinyl lactam and maleic anhydride, and an alkylvinylether, maleic anhydride and an N-vinyl lactam, said polymers being modified by an N,N-dialkylaminoalkylamine or an N,N-dialkylaminoalkanol.

2. The composition according to claim 1, wherein said cationic polymer is present in a proportion of between 0.05 and 20% of the total weight of the composition.

3. The composition according to claim 1, wherein said amphoteric polymer basically consists of the following repeating units:

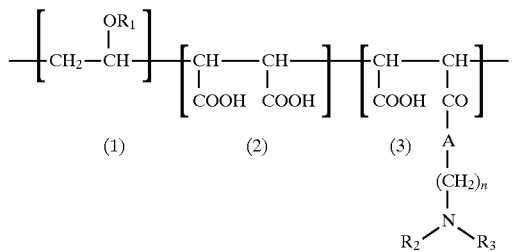

in which:
R$_1$ is a C$_1$–C$_6$ alkyl,
R$_2$ and R$_3$, whether identical or different, represent a C$_1$–C$_8$ alkyl,
A is an atom of oxygen or NH, and n=2 to 10.

4. The composition according to claim 3, wherein, in the repeating units of the amphoteric polymer, R$_1$, R$_2$, and R$_3$ represent —CH$_3$, A is NH, and n=3.

5. The composition according to claim 1, wherein said amphoteric polymer basically consists of the following repeating units:

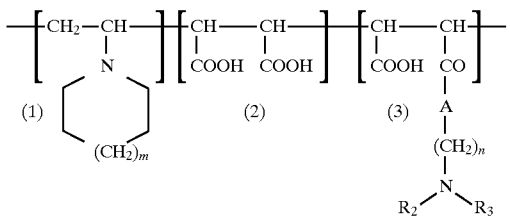

where:

R$_2$, R$_3$, A, and n have the same meanings as those given in claim 3, and m is 0, 1, or 2.

6. The composition according to claim 1, wherein said amphoteric polymer basically consists of the following repeating units:

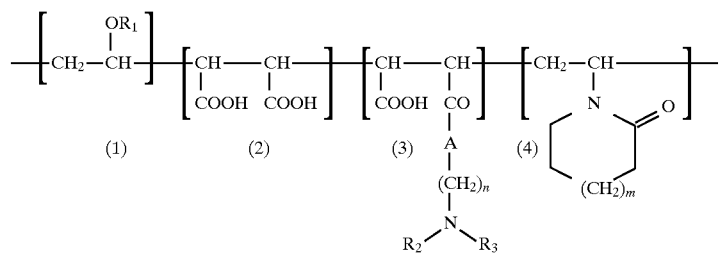

where:
R$_1$, R$_2$, R$_3$, A, m and n have the same meanings as those given in claim 3, and m=0, 1, or 2.

7. The composition according to claim 6, wherein, in the amphoteric polymer, R$_1$, R$_2$, and R$_3$ represent —CH$_3$, A is NH, n=3, and m=2.

8. The composition according to claim 1, wherein said amphoteric polymer is present in zwitterionic form.

9. The composition according to claim 1, wherein said amphoteric polymer is present in a proportion of between 0.05 and 20% of the total weight of the composition.

10. The composition according to claim 1, wherein the weight ratio of the cationic polymer to the amphoteric polymer ranges between 10/90 and 90/10.

11. The composition according to claim 1, wherein said cosmetically acceptable vehicle is an aqueous or hydroalcoholic solvent.

12. The composition according to claim 1, wherein said composition further contains conventional cosmetic additives selected from the group consisting of coloring agents, preservatives, sequestering agents, pH-adjustment agents, perfumes, silicones, proteins, sunscreens, treating agents and electrolytes.

13. The composition according to claim 12, wherein the pH-adjustment agent is selected from the group consisting of 2-amino-2-methyl-1-propanol, monoethanolamine, triethanolamine, triisopropanolamine, sodium, and potassium hydroxide.

14. The composition according to claim 1, wherein the composition pH is between 4 and 9.

15. A cosmetic composition for hair-care foams containing in a cosmetically-suitable vehicle, a mixture (i) of at least one cationic polymer selected from the group consisting of cationic celluloses, cellulose ethers containing quaternary ammonium groups, quaternized or non-quaternized vinyl pyrrolidone/dialkylaminoalkyl acrylate or methacrylate copolymers, and quaternized or non-quaternized vinyl pyrrolidone/dialkylaminoalkyl acrylamide or methacrylamide copolymers; and (ii) of at least one amphoteric polymer selected from the group consisting of polymers deriving from the copolymerization of an alkylvinylether and maleic anhydride, an N-vinyl lactam and maleic anhydride, and an alkylvinylether maleic anhydride and an N-vinyl lactam, said polymers being modified by an N,N-dialkylaminoalkylamine or an N,N-dialkylaminoalkanol; and a propellant selected from the group consisting of compressed air, carbon dioxide, nitrogen, nitrous oxide, butane, isobutane, dimethylether, chlorinated and/or fluorinated hydrocarbons and mixtures thereof.

16. The composition according to claim 15, wherein the foam obtained has a density of less than 0.25 g/cm$^3$.

* * * * *